United States Patent [19]

Iglesia et al.

[11] Patent Number: 5,118,715
[45] Date of Patent: Jun. 2, 1992

[54] SELECTIVE FIXED-BED FISCHER-TROPSCH SYNTHESIS WITH HIGH SURFACE AREA CU AND K PROMOTED, IRON/MANGANESE SPINELS

[75] Inventors: Enrique Iglesia, Clinton; Stuart L. Soled, Pittstown; Rocco A. Fiato, Basking Ridge; Joseph E. Baumgartner, Califon, all of N.J.

[73] Assignee: Exxon Research and Engineering Company, Florham Park, N.J.

[21] Appl. No.: 576,251

[22] Filed: Aug. 31, 1990

Related U.S. Application Data

[63] Continuation-in-part of Ser. No. 321,707, Mar. 10, 1989, abandoned, which is a continuation-in-part of Ser. No. 179,980, Apr. 11, 1988, abandoned, which is a continuation-in-part of Ser. No. 813,582, Dec. 26, 1985, Pat. No. 4,621,102, which is a continuation-in-part of Ser. No. 564,464, Dec. 20, 1983.

[51] Int. Cl.$^5$ .............................................. C07C 1/04
[52] U.S. Cl. ..................................... 518/713; 311/720
[58] Field of Search ................................. 518/713, 720

[56] References Cited

U.S. PATENT DOCUMENTS 4,547,525 10/1985 Kim ..................................... 518/713
4,621,102 11/1986 Fiato et al. .......................... 518/713

Primary Examiner—Howard T. Mars
Attorney, Agent, or Firm—Jay Simon

[57] ABSTRACT

Pelletized, high surface area, Cu and Group IA or IIA dual metal promoted Mn-Fe spinels which are reduced and operated in a fixed-bed reactor provide exceptionally high catalytic activity and selectivity in the conversion of $CO/H_2$ to high molecular weight hydrocarbons. These copper and Group IA or IIA metal promoted iron-manganese catalysts maintain good activity and selectivity to $C_5+$ hydrocarbons, and give low selectivity to CO2.

17 Claims, No Drawings

SELECTIVE FIXED-BED FISCHER-TROPSCH SYNTHESIS WITH HIGH SURFACE AREA CU AND K PROMOTED, IRON/MANGANESE SPINELS

This application is a continuation-in-part of U.S. Ser. No. 321,707 filed Mar. 10, 1989, now abandoned which is a continuation-in-part of U.S. Ser. No. 179,980 filed Apr. 11, 1988, now abandoned which is a continuation-in-part of U.S. Ser. No. 813,582 filed Dec. 26, 1985 now U.S. Pat. No. 4,621,102 which is a continuation in part of U.S. Ser. No. 564,464 filed Dec. 20, 1983 now abandoned.

BACKGROUND OF THE INVENTION

1. Field of the Invention

This invention relates to new, dual promoted, high surface area, iron/manganese spinel compositions promoted with copper and with a Group IA or Group IIA metal, their preparation and use. More particularly, this invention relates to new, unsupported, single phase Fe-Mn spinel compositions, dual promoted with copper and a Group IA or Group IIA metal, their preparation and use as pelletized catalysts in fixed-bed Fischer-Tropsch process for producing $C_5+$ hydrocarbons from mixtures of CO and $H_2$. These catalysts have a surface area greater than about 30 $M^2/g$ in which the atomic ratio of Fe to Mn is greater than 2:1.

2. Background of the Disclosure

Fischer-Tropsch processes have long been known to produce gaseous and liquid hydrocarbons containing $C_2$-$C_4$ olefins. Because of the importance of $C_2$-$C_4$ olefins, particularly as feedstocks for the chemical industry, modifications of the Fischer-Tropsch process are constantly being pursued toward the goals of maximizing $C_2$-$C_4$ olefin selectivity with the particular objective of maintaining high catalyst activity and stability under the reaction conditions and with iron based catalysts, in minimizing selectivity to $CO_2$. The main thrust of the efforts in this area has been in the area of catalyst formulation.

Coprecipitated and/or supported iron-based catalysts, including those containing manganese, are known for producing $C_2$-$C_4$ olefins. Examples of disclosures in the art directed to such iron-manganese catalysts and/or alloys include: W. L. vanDijk, et al., *Appl. Catal.*, 2, 273 (1982); Eur. Pat. Appl. 49888 to Ruhrchemie (1981); H. J. Lehman, 73rd AIChE Meeting Paper #103D; W. D. Deckwer, et al., *Chem. Ing. Tech.*, 53 (10), 818 (1981); V. Rao and R. Gormley, *Hydrocarbon Processing*, November (1981); H. Kolbel and K. Tillmetz, U.S. Pat. No. 4,177,203 (1970); EPO Patent Publication 0,071,770; U.S. Pat. No. 2,605,275; U.S. Pat. No. 2,850,515; *Prepr. Div. Pet. Chem. Am. Chem. Soc.* (1978) 23(2) pp 513-20; *Intersoc. Energy Convers. Eng. Conf.* 1978, 13(1) pp 482-6; U.S. Pat. No. 4,186,112; Ep 49,888; React. Kinet. Catal. Lett. 1982, 20(1-2) pp 175-80; U.S. Pat. No. 2,778,845; *Khim.* (1) *Tekhnol. Tooliv i Masel* (Russ.) 10(6) 5-10 (1965); UK Patent Appln. 2,050,859 A; German Patent Appln. DT 2919-921; *Prace Ustavu Vyzkum Paliv* 8, p. 39-81 (1964) (Czech).

An iron-manganese spinel of the formula, $Fe_2MnO_4$, is reported as a catalyst component formed during Fischer-Tropsch synthesis in which a coprecipitated Fe/Mn oxide catalyst is initially employed in *Applied Catalysis* 5 (1983) pp. 151-170.

U.S. Pat. No. 2,778,845 to McGrath, et al. discloses a non-spinel type, low surface area, sintered catalyst composition containing reduced or metallic iron as a major component. These compositions are used to synthesize hydrocarbons from mixtures of hydrogen and carbon monoxide and are formed via a high temperature fusion in an electric arc furnace. The sintered or fused composition must then be reduced, preferably in hydrogen, to form the metallic iron-containing catalyst. U.S. Pat. No. 2,605,275 to Kearby, et al. discloses forming hydrocarbons from mixtures of CO and $H_2$ employing low surface area, sintered, spinel type catalysts containing iron and a divalent metal of the general formula $Fe_2MeO_4$ wherein Me is the divalent metal. The molar ratio of Me to $Fe_2O_3$ is preferably greater than 1:1. Thus, the ratio of Fe/Me is no greater than 2/1 and preferably less than 2/1.

U.S. Pat. No. 3,970,738 to Matsui, et al. discloses an iron oxide composition containing a minor amount of manganese oxide and a process for making same. The object of the invention in this disclosure is stated as being able to provide iron oxide products substantially free from manganese compounds as impurities. The upper limit on the manganese component of these iron oxide products is taught and claimed as being less than 0.2 weight percent calculated as MnO. Maiti, et al. in "Iron/Manganese Oxide Catalysts for Fischer-Tropsch Synthesis. Part I: Structural and Textural Changes By Calcination, Reduction and Synthesis", J. Applied Catalysis, v5, p. 151-170 (1983) discloses the use of iron-manganese containing catalysts in a Fischer-Tropsch process to produce olefins. Spinel compositions are suggested as being present in the catalysts used in this reference. This reference does not disclose the use of copper and potassium promoted spinels, or synthesis of higher hydrocarbons.

Van Dijk, et al. in "Effects of Manganese Oxide and Sulfate on the Olefin Selectivity of Iron Catalysts in the Fischer-Tropsch Reaction", J. Applied Catalysis, v2, p. 273-288 (1982) disclose a Fischer-Tropsch catalyst which, on page 277, is set forth as a mixture of alpha iron oxide, alpha iron hydroxide and $Mn_2O_3$. This reference discloses that these catalysts produce substantially more than about 20% methane make and an equilibrium methane selectivity (on page 283) of over 30%. U.S. Pat. No. 4,177,203 to Kolbel, et al. discloses, in line 6-9 of column 3, a Fischer-Tropsch process using a catalyst which contains more than 50% manganese and less than 50% iron. This process produces low molecular weight olefins. Kolbel, et al. in "Feedstock For Chemical Industry By Selective Fischer-Tropsch-Synthese", 1978 Society of Automotive Engineers, p. 482-486, disclose a Fischer-Tropsch catalyst consisting of a precipitated mixture of gamma $Mn_2O_3$ and alpha $Fe_2O_3$ inserted in the manganese oxide lattice. Thus, the catalyst composition of this reference consists of mixed oxide phases. Further, the ratio of manganese to iron oxide of the catalyst disclosed therein is set forth as being between 8 and 10.

European Patent 71,770 discloses iron-manganese catalysts promoted with potassium, wherein the maximum ratio of iron to manganese is 1:2. Compositions set forth in the Tables on pages 11 and 13 of this reference disclose iron/manganese ratios of 1:3.

Bruce, et al. in "Light Olefin Production From $CO/H_2$ Over Silica Supported Fe/Mn/K Catalysts Derived From a Bimetallic Carbonyl Anion, $[Fe_2Mn(CO)_{12}]$", React. Kinet. Catal. Lett., v. 20, Nos. 1-2, p.

175-180 (1982) disclose olefin production using supported catalysts prepared from carbonyl precursors, with silica being the support. Methane selectivity incurred with the use of this catalyst in Fischer-Tropsch hydrocarbon synthesis reactions is disclosed as about 31% (unpromoted) and 18% (potassium promoted).

Jenson, et al. in "Studies on Iron-Manganese Oxide Carbon Monoxide Catalysts; I. Structure of Reduced Catalyst", J. of Catalysts, v. 92, p. 98-108 (1985) disclose iron-manganese catalysts showing enhanced selectivity for low molecular weight olefins from synthesis gas. The reduced catalyst composition is disclosed as having been found to be an alpha iron oxide and a manganese (II oxide) as separate phases, with the manganese oxide phase containing some divalent iron oxide in solid solution. Maiti, et al. in "Iron/Manganese Oxide Catalysts For Fischer-Tropsch Synthesis. Part II, Crystal Phase Composition, Activity and Selectivity" J. Appl. Catal. 16 (2) 215-25 (1985) disclose structural changes in the Fe-Mn oxide system under synthesis gases as a function of various pretreatments.

French Patent 2,554,433 discloses passing a mixture of $H_2$ and CO over a spinel catalyst having the general formula of $Li_xCu_{1-x}Fe_5O_8$ and French Patent 2,553,399 discloses a similar process employing a catalyst having the general formula of $Cu_xMn_{1-x}Fe_yCr_{1-y}O_4$.

U.S. Pat. No. 4,621,102 discloses the catalyst used in this process. However, the process disclosed in that patent is a slurry process wherein the catalyst particle size is indicative of slurried iron catalyst particles, that is, less than about 50 μm.

Finally, Pennline, et al. in "The Effect of Activation and Promotion on a Fischer-Tropsch Catalyst" 189th ACS National Meeting (Miami Beach 4-28-5/3/85) ACS Div. Fuel Chem. Prep. 30# 2:310-17 (1985) disclose a Fischer-Tropsch catalyst employed in a slurry reactor employing catalysts containing 21% iron 79% manganese oxide activated in-situ, under various conditions.

However, none of the references cited above describe a Fischer-Tropsch hydrocarbon process employing an unsupported single phase Fe/Mn spinel catalyst having an Fe:Mn atomic ratio above 2:1 and a surface area greater than about 30 $M_2/g$ and being dual promoted with both copper and a Group IA or IIA metal promoter agent.

Co, Ru and Fe catalysts are used to produce high molecular weight hydrocarbons from CO and $H_2$ in fixed bed reactors. Co and Ru do not catalyze the water-gas shift reaction (CO+$H_2O$ →$CO_2$+$H_2$) at synthesis temperatures, while Fe catalysts do ($CO_2$ selectivity >30%). Fe catalysts produce a more olefinic product, but high recycle ratios are required to decrease the $CO_2$ production rate. It is very desirable to develop Fe-based catalysts that can produce high $C_5+$ yields with low shift selectivity.

Iron catalysts coming close to fulfilling these requirements are used commercially at SASOL. These are Fe-based catalysts promoted with Si, K, and Cu; they are reported to produce ~20% $CO_2$ and high molecular weight products. Mn is apparently not a crucial component in such catalysts. Our uniquely prepared, high surface area Fe-Mn spinels, show unexpected and desirable behavior. They are the subject of a recently filed patent application (U.S. Ser. No. 814,040, filed Dec. 27, 1985) that describes their use as fine powders in a slurry reactor to produce $C_5$-$C_{15}$ α-olefins from CO and $H_2$.

In slurry reactors, these catalysts convert 40% of the feed CO to $CO_2$ at 270° C., 75 psi, and 2/1 $H_2$/CO. Other researchers have reported that Fe-Mn catalysts prepared differently from these can be useful to produce $C_2$-$C_4$ olefins from CO and $H_2$; they do not report low shift activity or high $C_5+$ selectivities. The instant invention teaches the unusual combination of low shift activity, low $CH_4$ selectivity and high $C_5+$ yields using pelletized high-surface area Fe/Mn spinels, promoted with K and Cu, and run in fixed bed reactors at low temperature (200°-240° C.), and high pressure (150-450 psi).

SUMMARY OF THE INVENTION

The present invention relates to pelletized relatively high surface area, unsupported, single phase, iron-manganese spinels which are dual promoted with both copper and a Group IA or IIA metal useful for selective synthesis of $C_5+$ hydrocarbons from mixtures of CO and $H_2$ in a fixed-bed process, said spinels having the empirical formula:

$Fe_xMn_yO_4$ wherein x and y are integer or decimal values, other than zero, with the proviso that the sum of x+y is 3 and the ratio of x/y is above 2:1, wherein said spinel exhibits a powder X-ray diffraction pattern substantially isostructural with $Fe_3O_4$, with said promoter metals being substantially deposited on the surface of said spinel and said surface area of said spinel being greater than about 30 $M^2/g$.

The catalyst compositions and attendant particle sizes of the instant invention provide greater catalytic activity and also greater selectivity towards $C_5+$ hydrocarbons with lower $CO_2$ selectivity in the fixed bed process described herein than similar compositions which are fully reduced and carbided for use in a slurry process disclosed in aforementioned U.S. Pat. No. 4,621,102. The $CO_2$ selectivity of the fixed bed process using the catalyst of this invention is less than about 30 vol.%, preferably less than about 20%, still more preferably less than about 15%

The high surface area catalyst compositions of this invention can be prepared by a process of adding an alpha-hydroxy aliphatic carboxylic acid, e.g., glycolic acid, to an acidic aqueous solution containing dissolved iron and cobalt salts and subsequently evaporating the solution to dryness to yield an amorphous, mixed metal glycolate, which, on calcining at elevated temperature, forms a mixed metal oxide exhibiting a spinel crystal structure and possessing a high surface area. The unsupported, high surface area Mn-Fe spinels prepared in this manner possess BET surface areas greater than 30 $M^2/g$. Typically, the spinels of this invention will have surface areas ranging between about 50-200 $M^2/g$.

This invention requires the use of a fixed bed in which the catalyst particles are at least an order of magnitude larger than slurried iron containing catalyst particles. Slurried iron catalysts are known in the prior art and are usually less than 50 μm in diameter, more likely in the range of 10-40 μm. Iron based slurry catalysts are typically in the 5-15 μm range.

The so-formed mixed metal oxide or spinel is then converted to the catalyst by contacting, at elevated temperature, with $H_2$ to form the reduced catalysts. Preferably the reduction is accomplished in-situ in a fixed-bed of catalyst pellets with an average diameter useful in a fixed bed process, that is, greater than 100 μm, preferably greater than 200 μm, still more preferably greater than 500 μm, and usually in the range 0.1 to 10 mm. (Larger size particles generally reduce the pressure drop in fixed bed processes.)

The spinels prepared according to the process of this invention may be promoted by surface impregnation or deposition with Group IA or Group IIA and copper metal salts prior to the reduction or other activation steps.

DETAILED DESCRIPTION OF THE INVENTION

The unsupported, high surface area, copper and alkali- or alkaline earth metal salt promoted iron-manganese single phase spinels of this invention are new compositions of matter which are isostructural with $Fe_3O_4$, as determined by X-ray diffractometry using copper K alpha radiation and exhibit a single spinel phase. By the term "spinel" is meant a crystal structure whose general stoichiometry corresponds to $AB_2O_4$, where A and B can be the same or different cations. Included within this definition is the commonly found spinel, $MgAl_2O_4$, A and B can have the following cationic charge combinations: $A=+2$, $B=+3$, $A=+4$, $B=+2$, or $A=+6$, $B=+1$. Spinels contain an approximately cubic close-packed arrangement of oxygen atoms with ⅛th of the available tetrahedral interstices and ½ of the octahedral interstices filled, and can exhibit hundreds of different phases. Further description of the spinel structure can be found in "Structural Inorganic Chemistry" by A. F. Wells, Third Edition, Oxford Press, and the Article "Crystal Chemistry and Some Magnetic Properties of Mixed Metal Oxides with the Spinel Structure" by G. Blasse, Phillips Research Review Supplement, Volume 3, pp 1-30 (1964). By the term "isostructural" is meant crystallizing in the same general structure type such that the arrangement of the atoms remains very similar with only minor change in unit cell constants, bond energies and angles. By the term "single phase spinel", as used herein, is meant one structural and compositional formula, corresponding to a single spinel material into which all of the metal components are incorporated, and exhibiting one characteristic X-ray diffraction pattern.

The catalyst of the instant invention is prepared by calcining a glycolate complex of iron and manganese as described in detail in U.S. Pat. No. 814,040. Ferric nitrate and manganese nitrate are dissolved in water, and mixed together. A second solution is prepared by adding to glycolic acid a sufficient amount of ammonium hydroxide to keep the pH of the resulting ammonium glycolate solution at about 6.5. The amount of glycolic acid is chosen such that the molar ratio of glycolic acid to iron plus manganese is about 1:1. The ammonium glycolate and iron-manganese nitrate solutions are combined, and the resulting solution on evaporation swells to form an amorphous mass. When heated between 175°–500° C. a high surface area (50–100 m²/gm) monophasic iron manganese spinel, isomorphous with magnetite forms. This spinel is promoted with 2% K and 1% Cu, pilled, and sieved to retain 150–500 particles (40–100 mesh).

The catalyst was then charged into a fixed bed reactor and run at the conditions described in the attached Tables. Table 1 compares the catalyst described here with the SASOL Fe-based catalysts. Table 2 compares the catalyst performance in fixed bed and slurry reactors. Space time yields and $C_5+$ are similar on the two catalysts, but $CO_2$ selectivities much lower on the Fe/Mn spinel, under identical reactor conditions.

The copper and Group IA or Group IIA metal promoted iron-manganese spinels of this invention possesses a BET surface area of over 30 $M^2/g$ and typically of from about 50–100 $M^2/g$ with about 75 $M^2/g$ being a general average surface area, as determined by the well-known BET surface area measurement technique as described in the reference *JACS* 60, p. 309 (1938) by S. Brunauer, P. H. Emmett, and G. Teller. This range of surface area generally corresponds to a particle size range of about 100 to 200 angstroms.

The spinel can be represented by the formula: $Fe_xMn_yO_4$, wherein x and y are decimal or integer values, other than zero, and wherein the sum of x plus y is 3, and the ratio of x to y is greater than 2:1, preferably being from above 2:1 to about 19:1. Particularly preferred is where the iron to manganese atomic ratio is about 3:1 to 7:1. The composition can further be comprised of a mixture of single phase spinels, of different iron-manganese atomic ratios.

Representative examples of the various spinels corresponding to the formula are $Fe_{2.85}Mn_{0.15}O_4$, $Fe_{2.625}Mn_{0.375}O_4$, $Fe_{2.25}Mn_{0.75}O_4$. A dual promoted spinel composition of the subject invention which is set forth in the Examples below is $Fe_{2.25}Mn_{0.75}O_4/2\%$ K, 1% Cu.

In general, the physical properties of the subject spinels of this invention are similar to those of magnetite and include melting point of above 1400° C., and a color of brownish-red. The dual promoted, iron-manganese spinels of this invention are used in unsupported form in $H_2/CO$ hydrocarbon synthesis.

Representative examples of suitable classes of the copper and Group IA and IIA metal promoter agents include carbonates, bicarbonates, organic acid and inorganic acid salts e.g. acetates, nitrates, halides, and hydroxide salts of copper and Group IA and IIA metals including lithium, sodium, potassium, cesium, rubidium, barium, strontium, magnesium and the like. The use of sulfate salts of the promoter metal should be avoided, because it has been found that the resulting catalyst will be inactive in the Fischer-Tropsch process.

Representative examples of specific promoter agents include copper carbonate, copper bicarbonate, copper nitrate, potassium carbonate, potassium bicarbonate, cesium chloride, rubidium nitrate, lithium acetate, potassium hydroxide, and the like. Group IA compounds are preferred with the copper with potassium being particularly preferred. The Group IA and IIA promoters will be present in an amount of from about a 0.1 to 10 gram-atom % of the total gram-atoms of metals present. A preferred level of promoter agent is in the range of 1 to 2 gram-atom % of the total gram-atom metal present. In the empirical formulas used herein, the amount of the promoter agent, e.g., potassium, is expressed in terms of gram atom percent based on the total gram-atoms of metals used. Thus, "1 gram-atom percent" of potassium signifies the presence of 1 gram-atom of potassium per 100 total gram atoms of combined gram atoms of Fe and Mn. Thus, the symbol "1% K" as used herein indicates 1 gram-atom percent potassium based on each 100 gram atom of the total gram atom of iron and manganese present.

The copper promoter metal will be present in the catalyst in an amount of from about 0.1 to 2.0 gram-atom percent based on the total metal content of the final catalyst composition and preferably from about 0.5 to 1.5 gram-atom percent.

The utility of these spinels is their ability upon subsequent reduction, preferably in-situ in a fixed-bed, to form active catalysts useful for making $C_5+$ hydrocarbons from $CO/H_2$ in a Fischer-Tropsch process with low $CO_2$ selectivity.

The pelletized and reduced forms of the above-described spinel are also subjects of this invention.

The copper and Group IA or IIA metal promoted spinels undergo unexpectedly facile in-situ reduction in a fixed-bed reactor, and pretreatment to form pelletized copper and Group IA or IIA metal promoted iron-manganese spinels in a reduced form, which are highly active in a Fischer-Tropsch process for making $C_5+$ hydrocarbons from $CO/H_2$.

The spinels can be made by a process in which an aqueous solution of manganese and iron salts of an alpha-hydroxy aliphatic carboxylic acid, is evaporated to dryness, leaving an amorphous residue, which is then heated at elevated temperature to substantially form the spinel, as a single spinel phase, being isostructural with $Fe_3O_4$ and possessing a surface area greater than 30 $M^2/g$, preferably above 50 $M^2/g$. The heating is conducted such that no significant loss in surface area of the final spinel is incurred.

The key to the synthesis of these high surface area spinels is in the use of an organic, saturated, aliphatic, alpha-hydroxy carboxylic acid to form a complex salt, which is soluble in the aforementioned aqueous medium, at a pH on the acidic side, i.e., pH of 5-7. The solubility of the iron and manganese organic salts of the alpha-hydroxy carboxylic acid prevent crystallization from occurring, which would result in a crystalline product being obtained from the solution, that would possess a relatively low surface area.

This method of preparation utilizes an alpha-hydroxy aliphatic carboxylic acid which acts as a solubilizing agent for the iron and cobalt salts in the aqueous solution. Any saturated aliphatic alpha-hydroxy carboxylic acid, containing at least one alpha-hydroxy grouping, can be used to form the soluble iron and manganese salts in the subject invention process in aqueous solution, is deemed to be included within the scope of this invention. Representative examples of such acids which can be mono-hydroxy or di-hydroxy or monocarboxylic or di-carboxylic are glycolic, malic, glyceric, mandelic, tartaric, lactic acids and mixtures thereof. A preferred carboxylic acid used in the process is glycolic acid.

The amount of acid used is at least the stoichiometric amount, i.e., 1 to 1 molar ratio for each metal present and preferably in about a 5-10% molar excess of the stoichiometric amount. Higher ratios can be used, if it is economical to do so. Lower amounts can also be used but would result in incomplete iron and cobalt acid salt formation.

The first step in the process comprises forming an aqueous solution by dissolving iron salts and manganese salts, in a water-soluble salt form such as their nitrates, sulfates, chlorides, acetates, and the like, in water.

The concentration of the salts in the aqueous liquid is not critical to the extent that the salts are present in less than a saturated solution to avoid precipitation. For example, an 80-90% saturated solution, of combined dissolved metal molarities for avoiding precipitation in the process, can be effectively used.

The temperature of the aqueous solution is not critical and may be above room temperature to aid in the solubilizing process. However, room temperature is adequate and is the temperature generally used in the process. The pressure also is not critical in the process and atmospheric pressure is generally used.

The aqueous solution can also contain a small amount of organic solvent such as ethanol, acetone, and the like for aiding in the solubilizing of the iron and manganese salts of the alpha-hydroxy carboxylic acid.

Following the dissolving of the iron and manganese salts, the alpha-hydroxy carboxylic acid is added, together with a sufficient quantity of base, usually being ammonium hydroxide, sodium hydroxide, potassium hydroxide, and the like, preferably ammonium hydroxide, to solubilizing the resulting acid salts. The amount of base added is sufficient to keep the pH in the range of about 5 to 7.0.

It should be noted that the exact sequence of steps need not be adhered to as described above, with the proviso that the resulting aqueous solution contain dissolved iron and manganese salts in stoichiometric amounts as iron and manganese salts of alpha-hydroxy carboxylic acid in solution. If there are any insoluble materials present after addition of the base and organic acid, they should be filtered prior to the evaporation step.

At this point, the resulting solution is evaporated, as for example, by air drying, or under reduced pressure, at elevated temperature, as practiced in a rotary evaporator, or in a vacuum drying oven.

The resulting material from the evaporation step is an amorphous residue, generally being a powder. This residue is heated at elevated temperature at 100° to 350° C. preferably 100°-200° C. and still more preferably 150°-200° C. for about 1 to 24 hours in generally air to result in a substantially single spinel phase which is isostructural with $Fe_3O_4$, as determined by X-ray diffractometry, as previously described herein. Preferred temperature range is 100°-400° C., and particularly preferred is about 350° C. for single phase spinel formation.

The dual promoted spinel is then pelletized, sieved to 40-100 mesh (150-500 microns) and reduced to form the catalyst. This particle size is convenient when operating laboratory scale/fixed bed reactors with internal diameters <0.5 in. (1.28 cm). For commercial size tube and shell reactors, the optimal catalyst size would be from 1000 to 10,000 μm (1 mm-10 mm) diameter particles The reduction is done by contacting the dual promoted spinel, at elevated temperature, with a suitable reactant such as $H_2$, or $H_2$ containing gas. Preferably the reduction and carbiding is accomplished simultaneously with a mixture of $CO/H_2$ with a $CO/H_2$ molar ratio of from about 1:10 to 10:1. A ratio of 1:2 has been found to be convenient in the laboratory. Still more preferably this reduction will be accomplished in-situ in a fixed-bed reactor.

The reduction step is generally conducted at a temperature of about 240°-290°C., or below and 255°-275° C. A preferred method of reducing the catalyst is after it has been pelletized and placed in the Fischer-Tropsch fixed-bed reactor. A particularly preferred method is where the promoted spinel is treated with a mixture of CO/hydrogen and reduced in-situ in one step prior to hydrocarbon synthesis. The pressure is generally about atmosphere, and a space velocity of about 20-20,000 v/v/hr is chosen in order to properly activate the iron present in the spinel.

The resulting pelletized and reduced catalyst is active for $C_5+$ hydrocarbon synthesis with lower $CO_2$ selectivity than is achieved with previously disclosed iron based Fischer-Tropsch catalysts.

Also, a subject of the instant invention is a fixed-bed Fischer-Tropsch process for producing $C_5+$ hydrocarbons by utilizing the Group IA or IIA metal and copper promoted iron-manganese spinel, and the reduced, Group IA or IIA metal and copper promoted iron-manganese catalyst described hereinabove.

The process mode for operating the Fischer-Tropsch process utilizing the catalysts described herein is a fixed-bed process wherein the catalyst is of an average particle size significantly larger than that used in slurry operations. The unique behavior of these large particle catalysts e.g. the significantly lower selectivity to $CO_2$ than that observed with smaller particle size slurry catalyst is demonstrated in subsequent examples. Fixed bed reactors for highly exothermic reactors such as CO hydrogenation are normally constructed with a large number of vertical tubes, typically with an internal diameter in the range of 1-6", located within a larger vessel (i.e. shell) through which a cooling medium is circulated. The desire to operate at high productivity, i.e. high volumetric $CO/H_2$ feed rates and to minimize the overall pressure drop along the catalyst containing tubes necessitates the use of relatively large diameter catalyst particles e.g. 1-10 mm diameter. This provides a void between particles that allow reactants and products to flow freely.

In the process, the hydrogen and CO are used in a molar ratio in the gaseous feedstream in about a 10:1 to 1:10 molar ratio, preferably 3:1 to 0.5:1, and particularly preferred 1:1 to 2:1 molar ratio.

The temperature used in the process of this invention will generally be at least about 190° C., i.e., 190°-270° C., preferably being 200 to 240° C., and particularly preferred 210°-230° C. Higher temperature ranges can also be used but tend to lead to lighter products and more methane. The pressure useful in the process of this invention will range between about 150 to 450 psig and preferably about 250 to 400 psig. Higher pressure can also be used but can lead to formation of high levels of condensed water which can retard activity.

The space velocity used in the process is generally about 100 to 20,000 volumes of gaseous feedstream/per volume of dry catalyst in the fixed-bed reactor/per hour and is preferably in the range of about 1,000 to 15,000 v/v/hr, more preferably 1,000-10,000 v/v/hr and still more preferably 5,000 to 10,000. Higher space velocities can also be used but tend to lead to lower % CO conversion, and lower space velocities can also be used but tend to lead to more paraffinic products.

The percent CO conversion obtainable in the subject process, while providing substantial quantities of $C_2-C_2O$ olefins, ranges from about 30 to 80 percent and usually about 50 to 60 percent for sufficient $C_2-C_2O$ olefin production.

"Total hydrocarbons" produced in the process is related to the selectivity of percent CO conversion to hydrocarbons being those hydrocarbons from $C_1$ to about $C_{40}$ inclusive. Total hydrocarbon selectivity is generally 0 to 80 percent and higher, of the total CO converted, and the remainder converted to $CO_2$.

The percent $C_2-C_{20}$ hydrocarbons of the total hydrocarbons produced including methane and above is about 60 to 90 wt%. The percent of $C_2-C_{20}$ produced is about 40 to 60 wt%. The olefins produced in the process are substantially alpha olefins.

The selectivity to methane based on the amount of CO conversion is about 1 to 10 weight percent of total hydrocarbons, produced. Preferably about 7 percent, and lower, methane is produced in the process.

As discussed above, the percent selectivity to $CO_2$ formation in the process is about 10 to 30 percent of CO converted, preferably less than about 20%. The unusually low $CO_{20}$ selectivity provided by the fixed bed catalyst and process of the instant invention provides significantly higher selectivity to $C_5+$ hydrocarbons than was heretofore possible with low cost iron based catalysts.

Preferably, the reaction process variables are adjusted to minimize $CO_2$ production, minimize methane production, maximize percent CO conversion, and maximize percent $C_2-C_2$ O olefin selectivity, while achieving activity maintenance in the catalyst system.

The effluent gases in the process exiting from the reactor may be recycled if desired to the reactor for further CO hydrocarbon synthesis.

Methods for collecting the products in the process are known in the art and include fractional distillation, and the like. Methods for analyzing the product liquid hydrocarbons and gaseous streams are also known in the art and generally include gas chromatography, liquid chromatography, high pressure liquid chromatography and the like.

This invention will be more readily understood by reference to the examples below.

EXAMPLES

Unless otherwise indicated, the selectivity weight percentages, based on carbon, of product hydrocarbons is given on a $CO_2$-free basis.

Catalyst Evaluation Under CSTR-Slurry Reactor Conditions

Into a slurry reactor, being a 300 cc Parr CSTR (continuous stirred tank reactor) wash charged: 72 g of octacosane and 0.5-8.0 g. of the spinel or catalyst being studied. The system was purged with nitrogen while the temperature was increased from room temperature to 200° C. The system was then placed under CO hydrogenation reaction conditions by adjusting the reaction temperature to 270° C., the $H_2/CO$ volume ratio to 2:1, the space velocity to 1500-24,000 V gaseous feedstream/V dry catalyst/hr, the pressure to 75 psig, and the slurry stirrer speed to 600 rpm in the octacosane solvent. The effluent gas from the reactor was monitored by an HP-5840A Refinery Gas Analyzer to determine percent CO conversion and the nature of the hydrocarbon products.

Preparation and Evaluation of High Surface Area $Fe_{2.25}Mn_{0.75}O_4$ Spinel 39.1 grams of ferric nitrate $(Fe(NO_3)_{3.9}H_2O)$ in 55 cc of water and 9.3 grams of manganese nitrate $Mn(NO_3)_{2.6}H_2O$ in 10 cc of water were mixed together. A solution was prepared by adding to 11.5 grams of 85% glycolic acid a sufficient amount of ammonium hydroxide such that the resulting pH of the ammonium glycolate solution was about 6.5. The ammonium glycolate solution constituted 0.129 moles of glycolic acid such that about a one to one molar ratio of iron and manganese metal to glycolic acid resulted. The ammonium glycolate solution was added to the aqueous solution containing iron and manganese salts and the contents stirred. The resulting solution was allowed to evaporate by air drying at room temperature.

The resulting dry solid was shown by X-ray diffraction to be an amorphous material because of lack of sharp, discrete reflections. The solid was heated in air at 175° C. for two hours. An X-ray diffraction pattern of the resulting material showed it to be a single phase, manganese/iron spinel isomorphous with $Fe_3O_4$. The X-ray diffraction peaks were broadened relative to a compositionally equivalent material obtained by a higher temperature procedure. This indicated that the resulting obtained material was of very small particle size. The surface area of the resulting material was about 100 square meters per gram.

The resulting material was then impregnated with (one or two) gram atomic percent of potassium using an aqueous solution of potassium carbonate and drying the resulting impregnated sample at 125° C. The resulting solid had an empirical formula of $Fe_{2.25}Mn_{0.75}O_4/2\%$ K. For the samples also containing the CU promoter, 1 gm atom % of Cu, via an aqueous copper nitrate solution was impregnated onto the sample which was then dried at 125° C.

EXAMPLE 1

The catalyst was then charged into a fixed bed reactor as a neat sample or diluted with quartz powder. The tubular reactor has a 0.5 inch internal diameter with a ⅛ inch outer diameter thermowell. In the dilution procedure, 2.0 grams of catalyst is added to quartz powder to a total volume of 15 cc. The catalyst is activated by first flushing the system with helium at room temperature followed by exposure to 2/1 $H_2/CO$ and subsequent heating to either 255°-260° C. or 275°-280° C. The catalyst is run at the conditions described in the attached Tables. Table 1 compares the catalyst described here with the SASOL Fe-based catalysts. Table 2 compares the catalyst performance in fixed bed and slurry reactors. Space time yields on $C_5+$ are similar on on the pelletized fixed-bed Fe/Mn spinel, under identical reactor conditions.

TABLE 1

COMPARISON OF SASOL CATALYST WITH CATALYST OF THIS INVENTION

|  | Fe/Mn/Cu/K Fixed-Bed | SASOL Fixed-Bed (Published) |
|---|---|---|
| Catalyst Activation (°C.) | 275–280 | n.a. |
| Metal-Time Yield ($h^{-1}$) | 3.8 | n.a. |
| Space-Time Yield ($H^{-1}$)($H_2$ + CO) | 1200 | 520 |
| Selectivity (%, $CO_2$-Free) |  |  |
| $CH_4$ | 3.5 | — |
| $C_2$-$C_4$ | 17.0 | — |
| $C_5+$ | 79.5 | 81 |
| $CO_2$ | 12.0 | 20 |
| Temperature (°C) | 229 | 232 |
| Pressure (psig) | 365 | 365 |
| Catalyst Mesh | 40–100 | — |

The superior performance of the process of the instant invention in terms of higher space time yield and lower $CO_2$ selectivity is demonstrated in this example relative to a commercially practiced catalyst.

TABLE 2

COMPARISON OF FIXED BED VERSUS SLURRY BED PERFORMANCE OF DUAL PROMOTED Fe—Mn CATALYSTS

| Reactor | fixed-bed | fixed-bed | slurry |
|---|---|---|---|
| Fe—time yield ($h^{-1}$) | 1.5 | 2.0 | 11.2 |
| Hours on Stream | 200 | 25 | 58 |
| CO conversion (%) | 30 | 50 | 69 |
| Selectivity (C-basis, %) |  |  |  |
| $CH_4$ | 4.5 | 8.6 | 1.1 |
| $C_2$-$C_4$ | 16.5 | 26.4 | 1.8 |
| $C_5+$ | 79.0 | 65.0 | 97.0 |
| $CO_2$ | 8.0 | 35.0 | 38.0 |
| % Olefin |  |  |  |
| $C_2$-$C_4$ | 73 | 82 | 93 |
| $C_{10}$ | 50 | 65 | 63 |
| Cat. Activation (°C.) | 255–260 | 255–260 | 270 |
| Temperature (°C.) | 228 | 263 | 270 |
| Pressure (psig) | 370 | 65 | 75 |
| Catalyst Mesh | 40–100 | 40–100 | >140 |

TABLE 3

EFFECT OF ACTIVATION TEMPERATURE ON FISCHER-TROPSCH ACTIVITY AND SELECTIVITY

|  | Fe/Mn/Cu/K Fixed-Bed | Fe/Mn/Cu/K Fixed-Bed |
|---|---|---|
| Activation Temperature* (°C.) | 255–260 | 275–280 |
| CO Conversion (%) | 30 | 48 |
| Metal-Time Yield ($h^{-1}$) | 1.5 | 3.8 |
| Space-Time Yield ($H^{-1}$)($H_2$ + CO) | 450 | 1200 |
| Selectivity (%, $CO_2$-Free) |  |  |
| $CH_4$ | 4.5 | 3.5 |
| $C_2$-$C_4$ | 16.5 | 17.0 |
| $C_5+$ | 79.0 | 79.5 |
| $CO_2$ | 8.0 | 12.0 |
| Temperature (°C.) | 228 | 229 |
| Pressure (psig) | 370 | 365 |
| Catalyst Mesh | 40–100 | 40–100 |

*Activation in $H_2/CO$ = 2/1. 65 psig. 24 h

The beneficial effect of activating the catalyst at low temperature is demonstrated with selectivity to $CO_2$ 25% lower than that achieved with an identical sample of catalyst activated at higher temperature.

TABLE 4

COMPARISON OF FIXED BED VERSUS SLURRY BED PERFORMANCE OF DUAL PROMOTED Fe—Mn CATALYSTS

| Reactor | fixed bed | fixed bed | slurry |
|---|---|---|---|
| Fe—time yield ($h^{-1}$) | 3.8 | 9.0 | 11.2 |
| Hours on Stream | 180 | 48 | 58 |
| CO conversion (%) | 48 | 43 | 69 |
| Selectivity (C-basis, %) |  |  |  |
| $CH_4$ | 3.5 | 9.5 | 1.1 |
| $C_2$-$C_4$ | 17.0 | 25.0 | 1.8 |
| $C_5+$ | 79.5 | 65.5 | 97 |
| $CO_2$ | 12.0 | 44.0 | 38 |
| % α-olefin |  |  |  |
| $C_2$-$C_4$ | 75 | 84 | 93 |
| $C_{10}$ | 55 | 67 | 63 |
| Cat. Activation (°C.) | 275–280 | 275–280 | 270 |
| Temperature (°C.) | 228 | 275 | 270 |
| Pressure (psig) | 365 | 65 | 75 |
| Catalyst Mesh | 40–100 | 40–100 | >140 |

This example sows the beneficial effect of operating the process of the instant invention at low temperature and high pressure with a pelletized catalyst. This provides high $C_5+$ selectivity combined with low selectivity to $CO_2$.

What is claimed is:

1. A hydrocarbon synthesis process for preparing a product containing $C_5+$ hydrocarbons and less than about 30% $CO_2$ comprising contacting in a fixed-bed a pelletized catalyst composition wherein the particle size is greater than about 200 microns average diameter, at a temperature of 200°–240° C., the catalyst comprising at least one unsupported, single phase, iron-manganese spinel dual promoted with both copper and a Group IA or IIA metal, said spinel exhibiting a single phase being isostructural with $Fe_3O_4$ as determined by powder X-ray diffractometry, and possessing a BET surface area greater than 30 $m^2/g$ and an Fe:Mn atomic ratio of at least 2/1, with a mixture of CO and hydrogen under conditions of pressure, space velocity, and elevated temperature for a time sufficient to produce said $C_5+$ hydrocarbons.

2. The process of claim 1 wherein said catalyst has been reduced prior to use.

3. The process of claim 1 wherein said spinel has been reduced and carbided prior to use.

4. The process of claim 1 wherein said hydrogen and CO are present in a hydrogen/CO molar ratio of 1:10 to 10:1.

5. The process of claim 1 wherein said temperature is in the range of about 210°–230° C.

6. The process of claim 1 wherein said pressure is in the range of about 150 to 450 psig.

7. The process of claim 1 wherein said space velocity is in the range of about 500 to 20,000 v/v/hr.

8. The process of claim 1 wherein the catalyst pellets have an average diameter greater than about 500 microns.

9. The process of claim 1 wherein the catalyst pellets have an average diameter of 1 to 10 mm.

10. The process of claim 1 wherein said iron and manganese are present in an iron-manganese atomic ratio of 2:1 or above and wherein said copper is present in an amount of from about 0.1 to 5 gram atom % of the iron manganese.

11. The process of claim 10 wherein said atomic iron-manganese ratio ranges from about 2:1 to 19:1.

12. The process of claim 10 wherein said spinel is of the formula: $Fe_xMn_yO_4$ wherein x and y are integer or decimal values, other than zero, wherein the sum of $x+y$ is 3 and wherein the ratio of x/y is from about 2:1 to 19:1.

13. The process of claim 12 wherein said spinel has an initial BET surface area of at least about 30 $m^2/g$.

14. The process of claim 10 wherein said a Group IA or IIA promoter agent present in said catalyst ranges from about 0.1 to 10 gram-atom percent of said total gram-atoms of Fe-Mn metals content.

15. The process of claim 14 wherein said promoter agent salt does not contain sulfate ions.

16. The process of claim 15 wherein said Group IA promoter agent is potassium carbonate.

17. The process of claim 16 wherein the catalyst pellets have an average particle diameter of 1 to 10 mm.

* * * * *